US010646672B2

(12) United States Patent
Kahlert

(10) Patent No.: US 10,646,672 B2
(45) Date of Patent: May 12, 2020

(54) POSITIVE PRESSURE PULSES CARDIO-PULMONARY RESUSCITATION DEVICE

(71) Applicant: KONINKLIJKE PHILIPS N.V., Eindhoven (NL)

(72) Inventor: Joachim Kahlert, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 246 days.

(21) Appl. No.: 15/738,266

(22) PCT Filed: Jun. 8, 2016

(86) PCT No.: PCT/EP2016/063017
§ 371 (c)(1),
(2) Date: Dec. 20, 2017

(87) PCT Pub. No.: WO2016/206979
PCT Pub. Date: Dec. 29, 2016

(65) Prior Publication Data
US 2018/0169360 A1 Jun. 21, 2018

(30) Foreign Application Priority Data
Jun. 26, 2015 (EP) .................................... 15173962

(51) Int. Cl.
A61M 16/00 (2006.01)
A61H 31/00 (2006.01)
(Continued)

(52) U.S. Cl.
CPC ........... A61M 16/022 (2017.08); A61B 5/486 (2013.01); A61H 31/006 (2013.01);
(Continued)

(58) Field of Classification Search
CPC ............ A61M 16/0006; A61M 16/009; A61M 16/022; A61H 31/006; A61H 2230/42; A61H 2230/425
See application file for complete search history.

(56) References Cited

U.S. PATENT DOCUMENTS 5,056,505 A   10/1991  Warwick
5,692,498 A   12/1997  Lurie
(Continued)

FOREIGN PATENT DOCUMENTS

EP     0029352 A1    5/1981
EP     1529547 A1    5/2005
(Continued)

OTHER PUBLICATIONS http://www.heart.org/HEARTORG/Conditions/More/CardiacArrest/Cough-CPR_UCM_432380_Article.jsp, date unavailable.

Primary Examiner — Valerie L Woodward
(74) Attorney, Agent, or Firm — Daniel H. Brean

(57) ABSTRACT

A cardiopulmonary resuscitation, CPR, device (100, 200, 400) for delivering intrathoracic pressure pulses to a subject (290), the device comprising an air pressure generator (110, 310, 410) for delivering air to the airways of the subject (290), wherein the air pressure generator (110, 310, 410) is configured to: operate a first mode, wherein in the first mode the air pressure generator (110, 310, 410) generates a first output (412, 770a, 770b) comprising a first plurality of positive pressure pulses (771) for temporally increasing the subject's intrathoracic pressure to induce compressions of the heart of the subject (290) by increasing the volume of the subject's lungs; operate a second mode, wherein in the second mode the air pressure generator (110, 310, 410) generates a second output (414, 880) comprising a second plurality of positive pressure pulses for providing an assured airflow to the lungs of the subject (290); and deliver a (Continued)

resulting output (425, 986, 1086) to the airways of the subject (290), the resulting output being the superposition of the first output (412, 770*a*, 770*b*) and of the second output (414, 880); wherein said first plurality of positive pressure pulses (771) have an amplitude greater than 30 mbar and a frequency in a range of 40-240 beats per minute; and wherein said second plurality of positive pressure pulses have an amplitude smaller than 30 mbar and a frequency in a range of 3 to 20 cycles per minute.

17 Claims, 11 Drawing Sheets

(51) Int. Cl.
*A61B 5/00* (2006.01)
*A61B 5/0245* (2006.01)
*A61B 5/083* (2006.01)
*A61B 5/087* (2006.01)

(52) U.S. Cl.
CPC .... *A61M 16/0006* (2014.02); *A61M 16/0009* (2014.02); *A61M 16/0096* (2013.01); *A61B 5/0245* (2013.01); *A61B 5/087* (2013.01); *A61B 5/0836* (2013.01); *A61H 2201/0176* (2013.01); *A61H 2201/0184* (2013.01); *A61H 2201/107* (2013.01); *A61H 2201/1207* (2013.01); *A61H 2201/1604* (2013.01); *A61H 2201/5007* (2013.01); *A61H 2201/5035* (2013.01); *A61H 2201/5071* (2013.01); *A61H 2230/04* (2013.01); *A61H 2230/06* (2013.01); *A61H 2230/205* (2013.01); *A61H 2230/42* (2013.01); *A61H 2230/425* (2013.01); *A61M 2016/0027* (2013.01); *A61M 2016/0039* (2013.01); *A61M 2230/06* (2013.01); *A61M 2230/432* (2013.01)

(56) References Cited

U.S. PATENT DOCUMENTS

| | | | |
|---|---|---|---|
| 5,988,166 A * | 11/1999 | Hayek | A61H 31/02 |
| | | | 128/202.12 |
| 6,708,690 B1 | 3/2004 | Hete | |
| 2003/0010344 A1* | 1/2003 | Bird | A61M 16/00 |
| | | | 128/205.24 |
| 2005/0051174 A1 | 3/2005 | Emerson | |
| 2005/0126578 A1 | 6/2005 | Garrison | |
| 2009/0171256 A1 | 7/2009 | Fiorina | |
| 2012/0118285 A1 | 5/2012 | Wondka | |
| 2014/0180036 A1 | 6/2014 | Bukkapatnam | |

FOREIGN PATENT DOCUMENTS

| | | |
|---|---|---|
| EP | 2198823 A1 | 6/2010 |
| WO | 2014111828 A1 | 7/2014 |

* cited by examiner

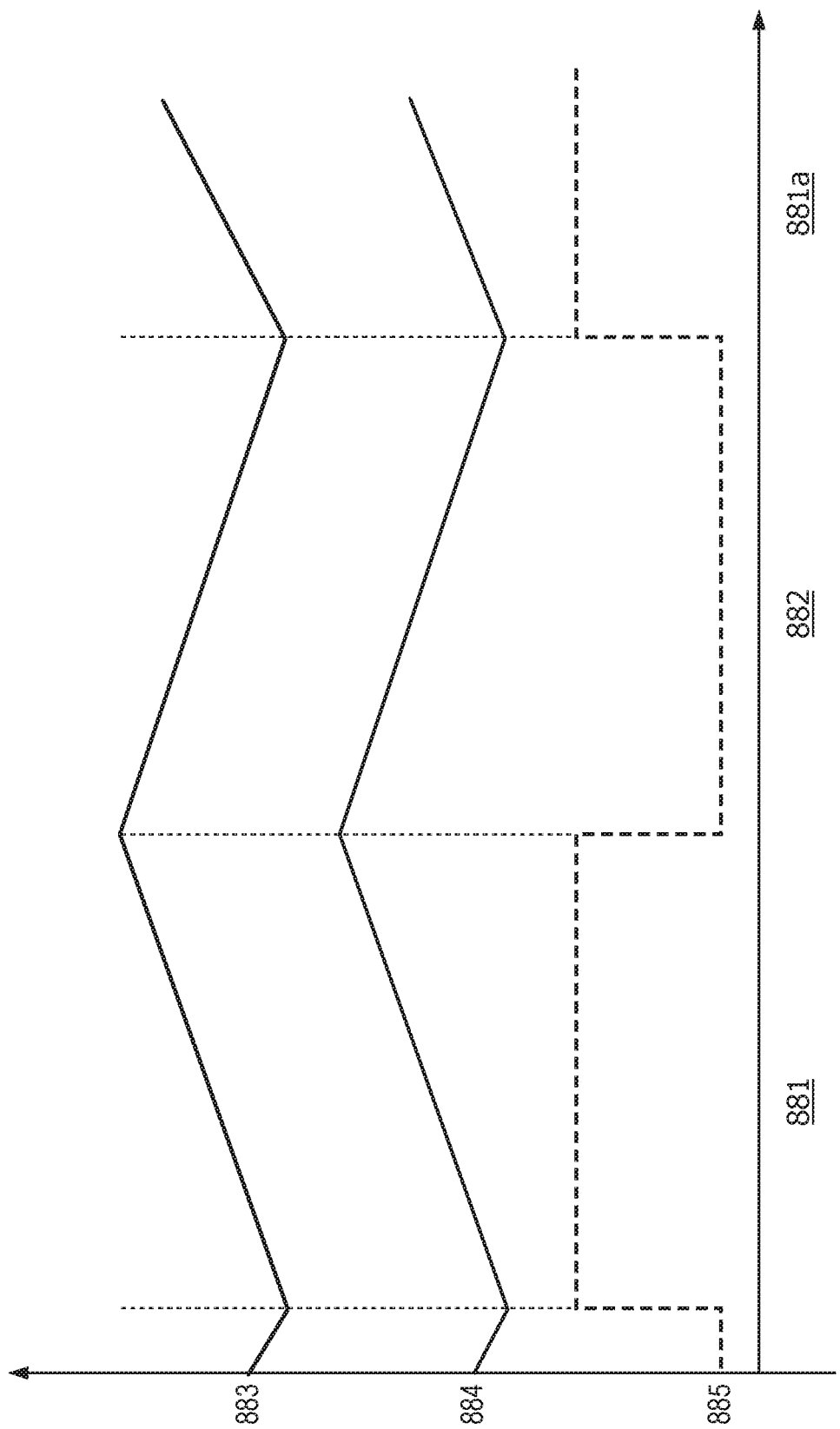

POSITIVE PRESSURE PULSES CARDIO-PULMONARY RESUSCITATION DEVICE

CROSS-REFERENCE TO PRIOR APPLICATIONS

This application is the U.S. National Phase application under 35 U.S.C. § 371 of International Application No. PCT/EP2016/063017, filed on Jun. 8, 2016, which claims the benefit of International Application No. 15173962.0, filed on Jun. 26, 2015. These applications are hereby incorporated by reference herein.

FIELD OF THE INVENTION

The present invention relates to a device and a method for providing Cardio-Pulmonary Resuscitation (CPR) to a subject by delivering air pressure pulses.

BACKGROUND OF THE INVENTION

Cardiopulmonary resuscitation (CPR) is an emergency procedure to restore blood circulation and breathing in a person who is in cardiac arrest or ventricular fibrillation. According to the resuscitation guidelines, CPR involves clearing and opening the patient's airway, providing rescue breathing (where the rescuer provides airflow by exhaling into the subject's mouth or nose) or ventilation with a manually operated bag-valve or powered portable ventilator apparatus for the patient, and applying chest compression at a rate of about 100 per minute in an effort to create artificial circulation in the systemic and pulmonary vessels. The external chest compression creates in the thorax a positive pressure on the heart and consequently presses blood from the heart chambers into the blood vessels. During the release of the chest compression the thorax recoils and permits a refilling of the heart chambers with venous blood. CPR may succeed in inducing a heart rhythm. CPR is continued until the patient has a return of spontaneous circulation (ROPC). If the spontaneous circulation is not re-established the person will die within a few minutes.

Ventilation is a key component of CPR during treatment of cardiac arrest. Venous blood returns to the heart from the muscles and organs depleted of oxygen (O2) and full of carbon dioxide (CO2), Blood from various parts of the body is mixed in the heart (mixed venous blood) and pumped to the lungs. In the lungs the blood vessels branch up into a net of small vessels surrounding tiny lung sacs (alveoli). The net sum of vessels surrounding the alveoli provides a large surface area for the exchange of gases by diffusion along their concentration gradients.

It is very difficult to perform consistent high quality manual CPR. Since CPR quality is key for survival there is a strong drive to have an automated device to replace less reliable and long duration manual chest compressions; in this regard, automated CPR (A-CPR) systems were introduced in the market recently.

Automatic ventilators capable of delivering desired airway pressures for use during CPR are also known. For example, U.S. Pat. No. 4,326,507 describes a combined chest compressor and ventilator that delivers a ventilation over a number of compression cycles and then delivers another series of compression cycles during the period between ventilations.

Known ventilation devices (also referred to in this context as ventilator, or resuscitator) do not function well while chest compressions are being applied. The known device follows a pre-determined, fixed ventilation procedure, and the person, e.g., a paramedic, who is applying the chests compressions to the patient, has to synchronize with this procedure. Applying chest compressions is a task that wears out any person very fast and the synchronizing quickly becomes harder and harder. Compressions of the chest may lead to high pressure peaks in the patient's airways that usually give rise to alarms in the ventilation device. If the person continues to apply the chest compressions asynchronously with the ventilation cycles of the ventilation device, there is a high probability that the positive ITP pressure during chest compression counteracts the positive pressure provided by the ventilation system which consequently prohibits an airflow into the lung. The typical dead space of the airway of adults is about 150 ml. If the ventilator cannot provide a tidal airflow volume higher than the dead space the CO2 enriched air cannot be exchanged by oxygen-rich air.

While the current American Heart Association recommendation is two consecutive ventilations every thirty compressions, that recommendation was promulgated in large part because it was found that the delays due to switching back and forth between compressions and ventilation by rescuers was resulting in insufficient levels of chest compressions and the resultant circulation. It is desirable, in the case of mechanical devices to integrate the functions of chest compressions and ventilations.

EP 0 029 352 discusses various CPR procedures for employing ventilation, and advocates a specific one thereof. This publication discloses an apparatus for conducting the specific CPR protocol. The apparatus comprises a combination of a reciprocal cardiac compressor means for cyclically compressing a patient's chest and a ventilating means for inflating the patient's lungs to a relatively benign limiting pressure over a period of time encompassing at least one cycle of the compressor means. Both the cardiac compressor and the ventilator of the CPR apparatus are pneumatically operated and pneumatically controlled.

A-CPR devices haven't been able so far to ensure the delivery of a CPR procedure capable of substituting manual CPR; the main problems are the difficulties in properly fitting the device to the patient, especially in situations in which it is not possible to rest the patient in a stable, flat surface. Moreover, the patient interface of the A-CPR itself needs to be adjusted to the patient size, which may substantially delay the procedure. Furthermore, the use of an A-CPR device in combination with a mechanical ventilator is even more complicated due to the encumbrance generated by two different devices, especially when the rescuer has to reach the patient in hard to reach locations.

US 2012/118285 A1 relates to a ventilator configured to provide ventilation therapy for persons suffering from respiratory and breathing disorders, such as respiratory insufficiency and sleep apnea. U.S. Pat. No. 5,988,166 A discloses another ventilator apparatus for assisting or producing ventilation of the lungs of a patient.

U.S. Pat. No. 5,056,505 A relates to chest compression devices, such as a chest compression vest, which aid in the loosening and elimination of mucus from the lungs of a person, particularly people affected by cystic fibrosis.

U.S. Pat. No. 5,692,498 A discloses devices and methods used in conjunction with external chest compression and decompression as a part of CPR procedures. In particular, the devices and methods disclosed therein aim at increasing cardiopulmonary circulation induced by chest compression and decompression when performing CPR.

US 2014/180036 A1 describes a wireless sleep apnea treatment system for predicting and minimizing, or averting, sleep apnea episodes.

SUMMARY OF THE INVENTION

It would be advantageous to have an automated CPR device which is easily and rapidly connected to the patient independently from the patient's size or position.

It is therefore an object of the present invention to provide a device and a method which address such concern. This object is solved by the CPR device of claim 1, the method of operating an air pressure generator of claim 16, and the computer program product of claim 17. Advantageous embodiments are defined in the dependent claims.

In a first aspect of the invention the object is achieved by a CPR device for delivering intrathoracic pressure pulses to a subject, the device comprising an air pressure generator for delivering air to the airways of the subject, wherein the air pressure generator is configured to:

operate a first mode, wherein in the first mode the air pressure generator generates a first output comprising a first plurality of positive pressure pulses for temporally increasing the subject's intrathoracic pressure to induce compressions of the heart of the subject by increasing the volume of the subject's lungs;

operate a second mode, wherein in the second mode the air pressure generator generates a second output comprising a second plurality of positive pressure pulses for providing an assured airflow to the lungs of the subject; and deliver a resulting output to the airways of the subject, the resulting output being the superposition of the first output and of the second output;

wherein said plurality of positive pressure pulses (PPP) have an amplitude greater than 30 mbar and a frequency in a range of 40-220 beats per minute, and wherein said second plurality of positive pressure pulses have an amplitude smaller than 30 mbar and a frequency in a range of 3 to 20 cycles per minute.

An advantage of the present invention is that it is possible, with the same device and the same patient interface, to deliver CPR and ventilation at the same time, as opposed to the current state of the art, in which CPR is delivered manually or by means of a device, and ventilation is provided by mouth to mouth respiration or by means of a different device.

In a second aspect, the object is achieved by a method of operating an air pressure generator for delivering intrathoracic positive air pressure pulses to a subject, wherein the air pressure generator is capable of operating in a first and second mode, wherein each mode is characterized by generating air pressure according to a specific output, said method comprising: activating a first operating mode, said first mode generating a first output; activating a second operating mode, said second mode generating a second output, wherein a resulting output generated by the air pressure generator is the superposition of the first output and of the second output, wherein said first output comprises a first plurality of positive pressure pulses for temporally increasing the subject's intrathoracic pressure to induce compressions of the heart of the subject by increasing the volume of the subject's lungs, said first plurality of positive pressure pulses having an amplitude greater than 30 mbar and a frequency in a range of 40-240 beats per minute, and wherein said second output comprises a second plurality of positive pressure pulses for providing an assured airflow to the lungs of the subject, said second plurality of positive pressure pulses having an amplitude smaller than 30 mbar and a frequency in the range of 3 to 20 cycles per minute. In the second mode the second output can either be flow controlled to assure a certain airflow during one cycle or can be pressure controlled to increase and decrease the second mode pressure according to a predefined protocol. The flow controlled mode is used in mechanical ventilation, that is, when the patient does not show spontaneous breathing, while the pressure controlled mode (such as a BiPAP protocol) is used when the spontaneous breathing is recovered, but the subject still needs an external support for breathing properly (assisted ventilation).

In a third aspect, the object is achieved by a computer program product comprising a computer readable medium having computer readable code embodied therein, the computer readable code being configured such that, on execution by a suitable computer, processor or controller that is for use with an air pressure generator for delivering intrathoracic positive air pressure pulses to a subject, the computer, processor or controller is caused to perform the method of the second aspect of the present invention.

It shall be noted that all embodiments of the present invention concerning a method, might be carried out with the order of the steps as described, nevertheless this has not to be the only and essential order of the steps of the method. All different orders and combinations of the method steps are herewith described.

The invention solves the aforementioned problem by providing a device which compresses the heart by repeatedly inflating the lungs, thus temporarily increasing the intrathoracic pressure (ITP), which in turn induces compression of the heart, because the heart shares the rib cage with the lungs. This is the same mechanism used by manual or automatic external CPR, wherein in traditional CPR the ITP is increased by reducing the volume of the rib cage (by compressing the chest), while according to the current invention the ITP is increased by increasing the lungs volume.

Moreover, since the ITP is increased by delivering air pressure pulses, the invention uses the same air pressure generator to deliver ITP pulses and assured airflow by mechanical or assisted ventilation.

In an embodiment of the device according to the first aspect, the air pressure generator is configured to operate the first mode and the second mode simultaneously.

In an embodiment of the device according to the first aspect, the device is arranged for receiving measured vital signs of the subject, the air pressure generator being arranged to deliver the first plurality of PPP and/or the second plurality of PPP in dependence of the measured vital signs. An advantage of such embodiment is that it is possible for example to set up the device so that it is capable of automatically adapting the delivery of PPP based on the conditions of the subject, as determined when receiving the measured vital sign. Furthermore, since the device can operate in different modes, it is possible to select the operating mode based on the received measured vital signs.

In another embodiment of the device according to the first aspect, the device is configured to interrupt delivering air pressure pulses of said first plurality for a predetermined time, in order to check whether the received vital sign is in a pre-determined range, and wherein the device is further configured to continue with delivering the air pressure pulses of said first plurality when the vital sign is not in the predetermined range during the predetermined time. An advantage of this embodiment is that it is possible to configure the device to automatically stop delivering CPR once the subject is not in need anymore.

In another embodiment of the device according to the first aspect, the air pressure generator is further configured to deliver a negative pressure pulse after a positive pressure pulse of said first plurality. An advantage of this embodiment is that it allows the heart to expand more easily after a compression.

BRIEF DESCRIPTION OF THE DRAWINGS

Exemplary embodiments of the invention will be described in the following drawings.

FIG. 8a is a graph showing the relationship between the flow delivered by a device according an embodiment of the invention and the variation in lung Volume and ITP during mechanical ventilation.

DETAILED DESCRIPTION OF EMBODIMENTS

Figure 1:
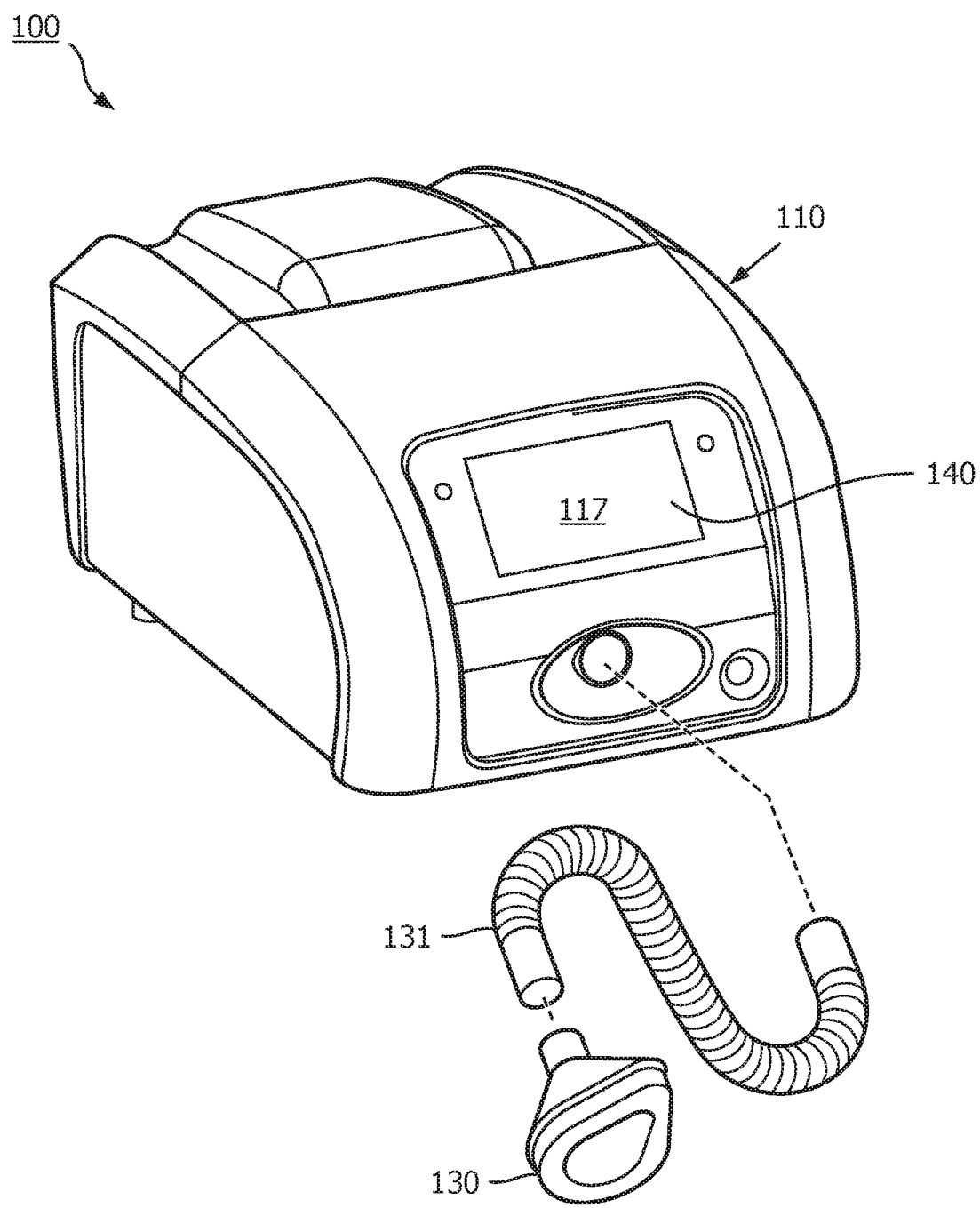
FIG. 1 is a schematic view of a device according to an exemplary embodiment of the invention.

The present invention is based on the insight of the inventor that coughing can induce heart compression and thus stimulate the blood flow when the heart is not properly functional. For example, during a sudden arrhythmia (abnormal heart rhythm), it may be possible for a conscious, responsive person to cough forcefully and repetitively to maintain enough blood flow to the brain to remain conscious for a few minutes until the arrhythmia is treated. Blood flow is maintained by increased pressure in the chest that occurs during forceful frequently repeated coughs (http://www.heart.org/HEARTORG/Conditions/More/CardiacArrest/Cough-CPR_UCM_432380_Article.jsp). Published cases report of people being able to maintain some sort of cardiac output during cardiac arrest by vigorous coughing—so-called "cough CPR". The scenario has usually been of a patient developing ventricular fibrillation or cardiac arrest whilst being monitored, often whilst undergoing cardiac catheterization. The patient had been encouraged to cough and a measurable circulation has been recorded and the heart started to beat regularly in sinus rhythm. This evidence supports the theory that chest compressions during CPR are successful because they repeatedly increase ITP, which causes compression of the heart and result in a flow of blood.

When voluntarily coughing, first the lungs are inflated by an intense inhalation, and then the muscles surrounding the thorax suddenly contract, pushing on the lungs and abruptly increasing the ITP (see also FIG. 5 and related description below); such increase in ITP violently forces the air out of the lungs, resulting in a cough stroke. At the same time, the heart is also subject to the same abrupt pressure increase, since it shares the space within the thorax with the lungs.

When coughing, the increase in ITP is due to the thoracic muscles compressing the lungs; however, the inventors of the present invention realized that the same effect could be obtained via an inversed mechanism, i.e. by forcing air into the lungs, which temporarily increases the ITP due to the fact that the anatomical structure and the mechanical properties of the chest muscles induce the thorax to expand more slowly than the lungs; the increased ITP is then transmitted to the heart, which is thus compressed. Therefore, if air would be forced into the lungs in a controlled manner, at a frequency similar to the frequency of traditional CPR, it should be possible to stimulate the blood flow similarly to how blood flow is stimulated by traditional CPR.

In the context of the present invention, a positive pressure pulse relates to the delivery to a subject of a certain airflow with a pressure profile characterized by a steep increase followed by a relatively short plateau, such plateau followed by a steep decrease of pressure. Such decrease does not necessarily need to be as steep as the increase, and the plateau can have different lengths; see also FIG. 7 and related description below.

In the context of the present invention, to mechanically ventilate a patient means to support or completely substitute the spontaneous respiration of the subject.

FIG. 1 shows a schematic view of the device 100 according to one embodiment of the invention. Device 100 comprises an air pressure generator 110, and it is designed to be connected to other components used when operating device 100. In particular FIG. 1 shows a patient interface 130, connectable to the device via tubing 131; sensor 140, which is attachable to a subject and is capable of sending a measured physiological signal to device 100 via an electric cable or wirelessly. Device 100 can also comprise a display 117 for showing information to the user. Air pressure generator 110 can comprise any kind of device capable of generating air pressure, for example a blower or a compressed air tank. In an embodiment, patient interface 130 is a full face mask which properly seals the nose and mouth. In another embodiment, patient interface 130 is equipped with a plurality of sensors 140; for example, an electrical sensor to measure the ECG, a pressure sensor coupled to the hose of the mask, a flow sensor, and a capnography device for analyzing the CO2 concentration of the exhaled air. However, any number and combination of sensor is within the scope of the present invention.

Figure 2:
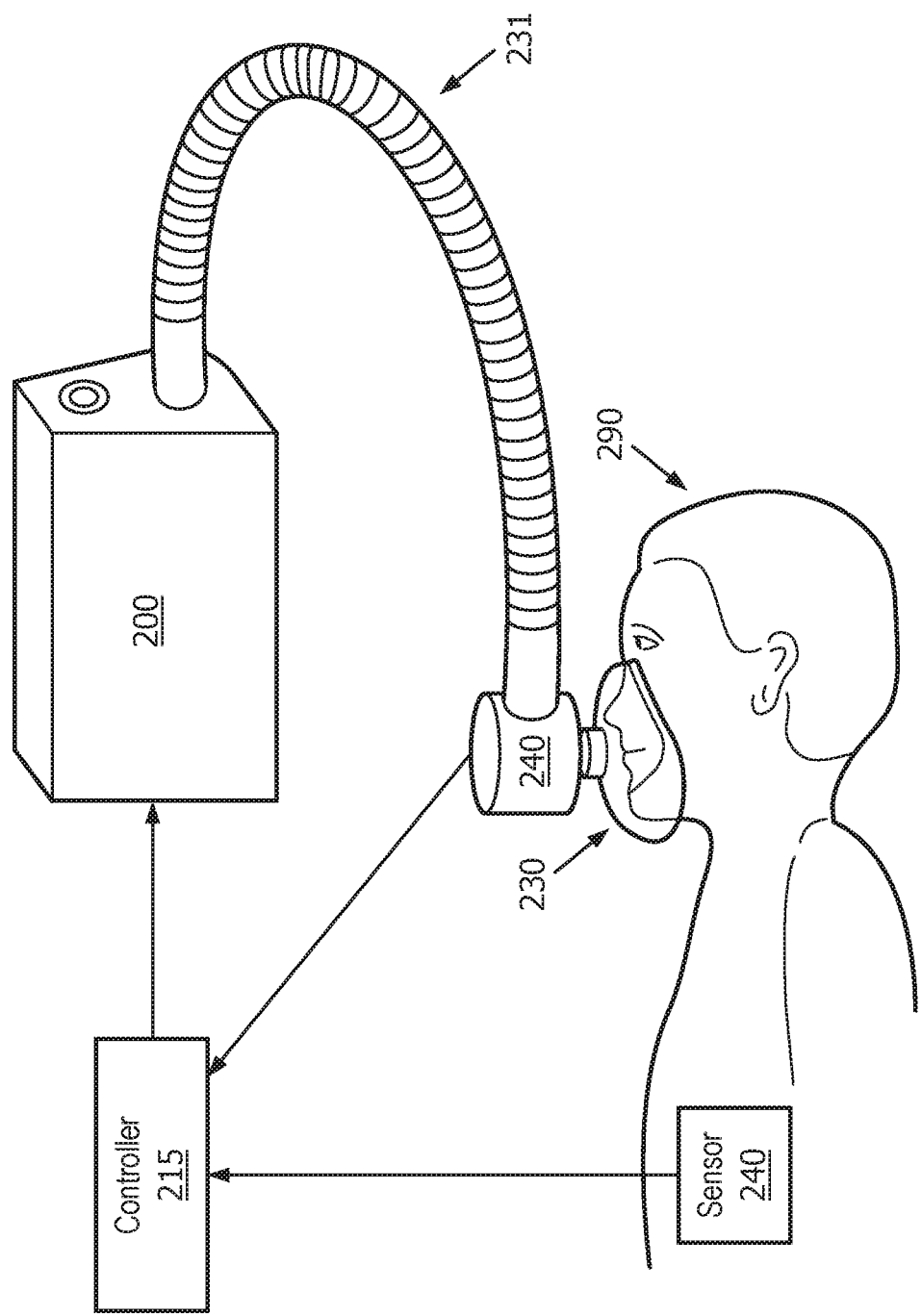
FIG. 2 is a schematic view of a device connected to a subject.

FIG. 2 shows a schematic view of a device 200, similar to previous device 100, when connected to a subject 290. Device 200 is coupled to subject 290 via patient interface 230 and tubing 231. Sensor 240 is applied on subject 290 and it is used to monitor the subject's vital signs, for example cardio and respiratory pattern. Sensor 240 is coupled to a controller 215 which is in turn connected to device 200. Sensor 240, patient interface 230 and controller 215 can be part of device 200, but they can also be separated from it, and any suitable component can be used. Device 200 according to this embodiment can be used as stand-alone CPR device to be used for delivering CPR to a subject undergoing cardiac arrest. Once the rescuers ascertain, for example via sensor 240 or via any other integrated or external sensor, that subject 290 is indeed undergoing cardiac arrest, they can apply patient interface 230 to subject's 290 airway and immediately start the CPR procedure, without any need for adapting the device to the subject's position or size. It is an advantage of the present invention that the CPR procedure according to the present invention can be performed in any body position of the person being supine, lateral or upright. Once activated, device 200 will deliver PPP at a predetermined frequency in the range of 40 to 240 beats per minute. Preferably, the operating frequency is chosen substantially similar to the averaged physiological heartrate of subject 290, for example 110 beats per minute for an adult person with a resting HR of 60 and a maximal HR of 160. In the context of the present invention, by "physiological CPR heartrate" it is intended the average heart rate of a person of similar age, gender and size of the patient to whom the invention is applied to. However, to better mimic the heartbeat, it is also possible to change the PPP frequency based on the subject's age; for example, the resting and maximal heart rate of a young child is higher than the heart rate of an elderly. When using device 200 according to this embodiment, subject 290 can be ventilated by different means, for example by means of a volume assured mechanical ventilator, a positive airway pressure (PAP) device or through mouth to mouth respiration. In an embodiment, the device can be set by default with predefined PPP settings adapted for an adult, middle age person, in order to reduce the time spent to adjust the settings.

Figure 3:
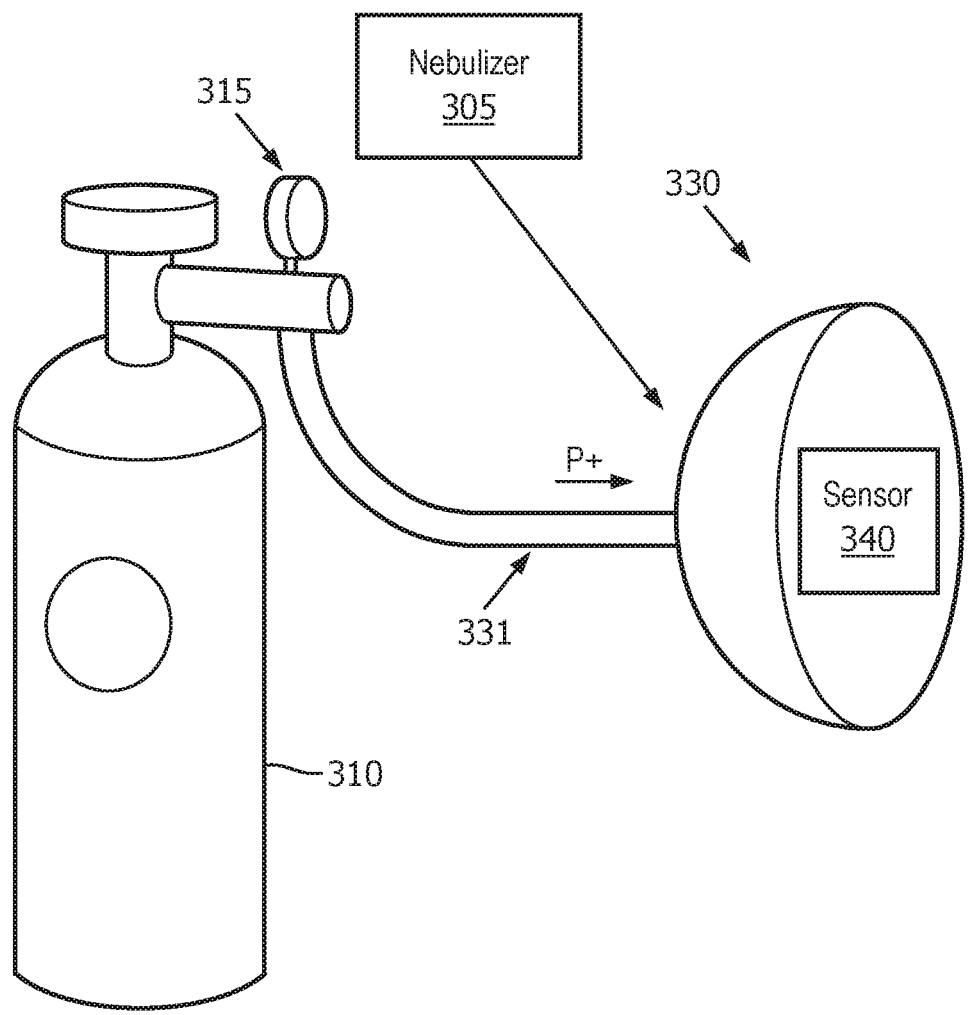
FIG. 3 is a schematic view of a device according to another exemplary embodiment of the invention.

FIG. 3 shows an alternative to the embodiment shown in FIG. 2, in which air pressure generator 310 comprises a compressed air tank 310, the output of which is controlled by controller 315. Air pressure generator 310 is coupled to a subject via tubing 331 and patient interface 330. An advantage of such embodiment is that an air tank can provide an airflow characterized by a different gas composition in comparison to atmospheric air; for example, an airflow with a higher oxygen concentration, or a nitric oxide (NO) supplement can be provided. As a further optional feature, the airflow may further comprise particles and aerosols provided by a nebulizer 305, for inducing a desired physiological effect specific for the situation and the subject, for example compounds to induce bronchodilation and facilitate ventilation.

In this embodiment, a sensor 340 is comprised in patient interface 330. It is intended that the alternatives to the air pressure generator and to the sensor shown in this FIG. 3, like compressed air tank 310 and sensor 340, can be implemented in all other embodiments of the invention.

It would be advantageous to have a single device for delivering CPR and mechanical ventilation or device assisted PAP at the same time, which is not cumbersome and therefore it is easy to carry to an emergency location, for example where a subject is undergoing a cardiac arrest episode.

Figure 4:
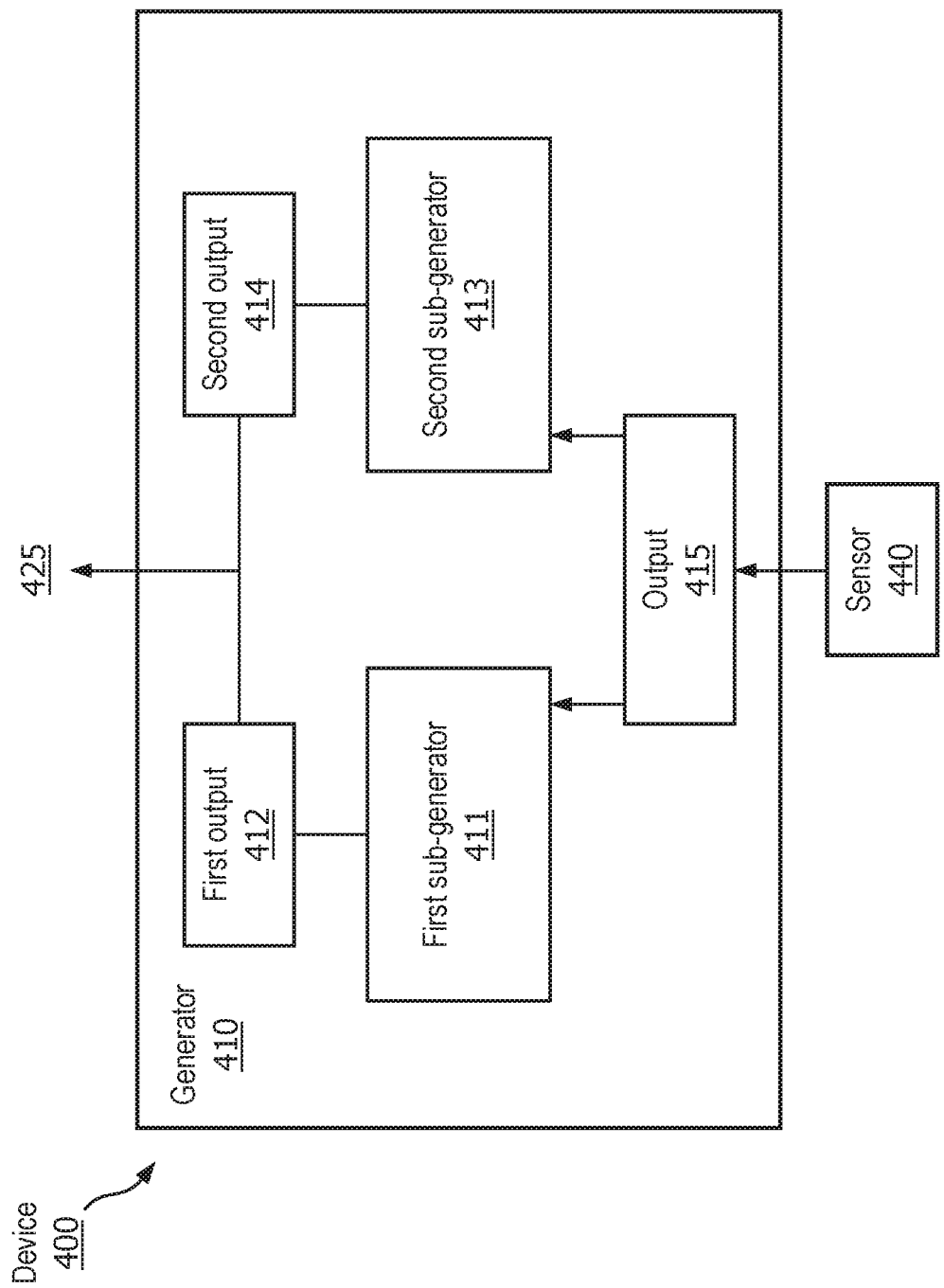
FIG. 4 is a schematic representation of a device according to another exemplary embodiment of the invention.

FIG. 4 schematically shows the invention according to another embodiment that aims at solving the aforementioned problem. According to the present invention, device 400 is used not only to deliver PPPs, but also for mechanically ventilating (or for providing assisted ventilation to) a subject. This can be achieved for example by an air pressure generator 410 comprising a controller 415 for controlling its operations based on a vital sign measurement received by sensor 440. Air pressure generator 410 comprises a first sub generator 411 capable of generating first output 412, and a second sub generator 413, capable of generating second output 414. Sub-generator 411 and 413 can each be dedicated to a different function, for example sub generator generates output 412 for delivering CPR and sub-generator 413 for generating output 414 for mechanically ventilating the subject; however, it is in the scope of the present invention that other combinations are possible; for example, it is possible to include additional sub-generators. According to the present invention, a single device 400 can perform both CPR and mechanical (or assisted) ventilation, i.e. the main operations required in the rescue of a subject undergoing a cardiac arrest episode. Device 400 can be further capable of ventilating a subject according to different known modalities, for example normal ventilation, in case the patient is not breathing spontaneously, and CPAP/BiPAP mode, in case a certain degree of spontaneous breathing is detected. One possible way of designing air pressure generator 410 so that it can deliver the two modes of operation is for example described in U.S. Pat. No. 6,708,690, herewith incorporated by reference. A possible method to operate air pressure generator 410 is herein described: the method comprises activating a first operating mode, said first mode generating a first output 412, wherein the activation of said first operating mode depends on a received vital sign, activating a second operating mode, said second mode generating a second output 414, wherein the activation of said second operating mode depends on a received vital sign, characterized in that the resulting output 425 generated by the air pressure generator is the superposition of the first output 412 and of the second output 414.

Figure 5:
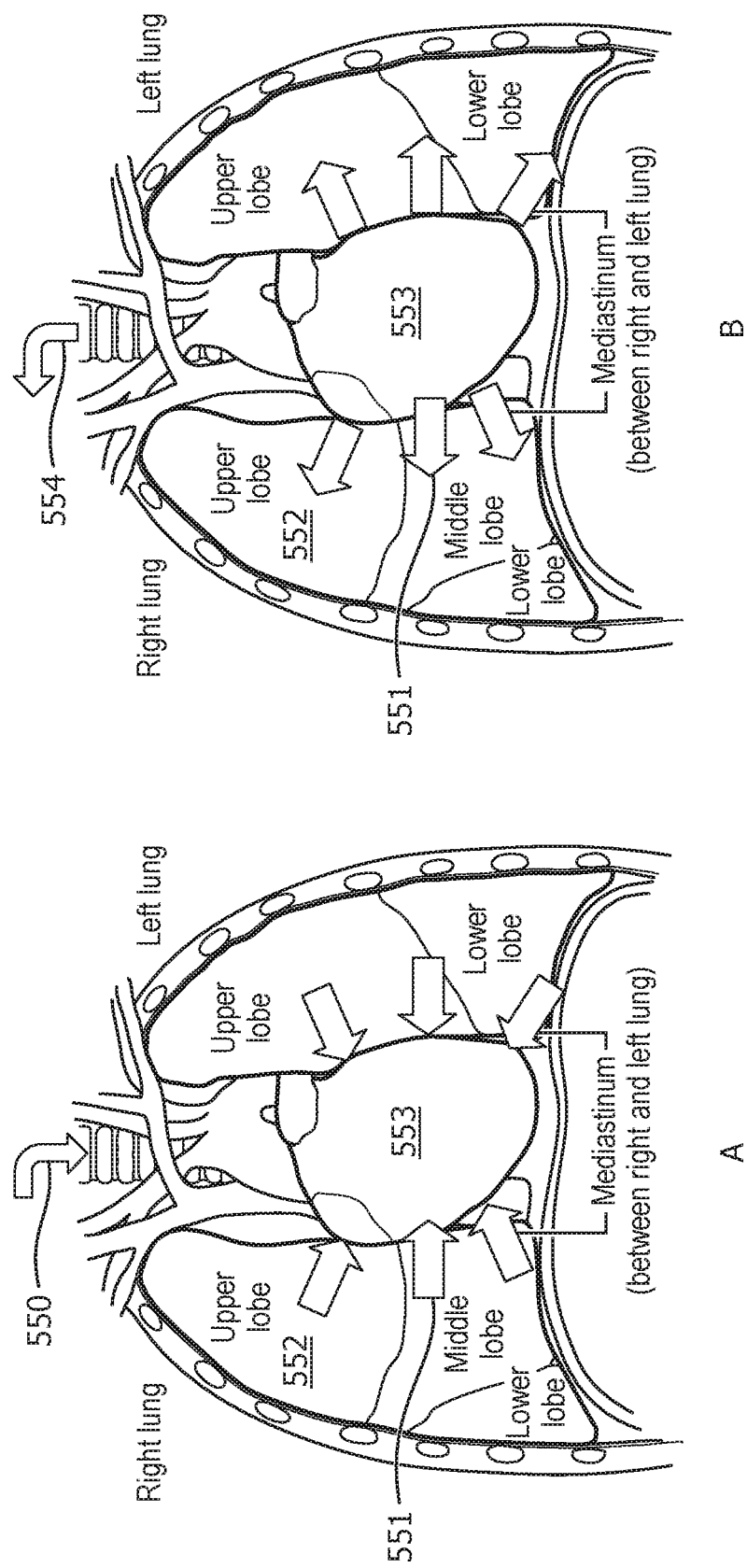
FIG. 5 is a schematic representation of the effect that variations in the ITP have on the heart.

FIG. 5 schematically shows how the PPPs generated by a device according to the present invention induce heart compression and thus blood flow in the subject. When a positive pressure pulse 550 is applied to lungs 552 of a subject (FIG. 5A), lungs 552 are inflated, thus increasing the ITP resulting in a compressing force being exerted to the heart 553, as indicated by arrows 551. When the heart is thus compressed, blood is pushed out of the heart and into the arteries, inducing an artificial circulation similar to the circulation generated by a manual chest compression.

Vice versa, when the pressure generated by the air pressure generator decreases (FIG. 5B), the air 554 inside the lungs is released back into the environment, so that the ITP also decreases, lungs 552 deflate and the heart is allowed to expand again, thus attracting venous blood into it and completing the artificially initiated heartbeat cycle.

Figure 6:
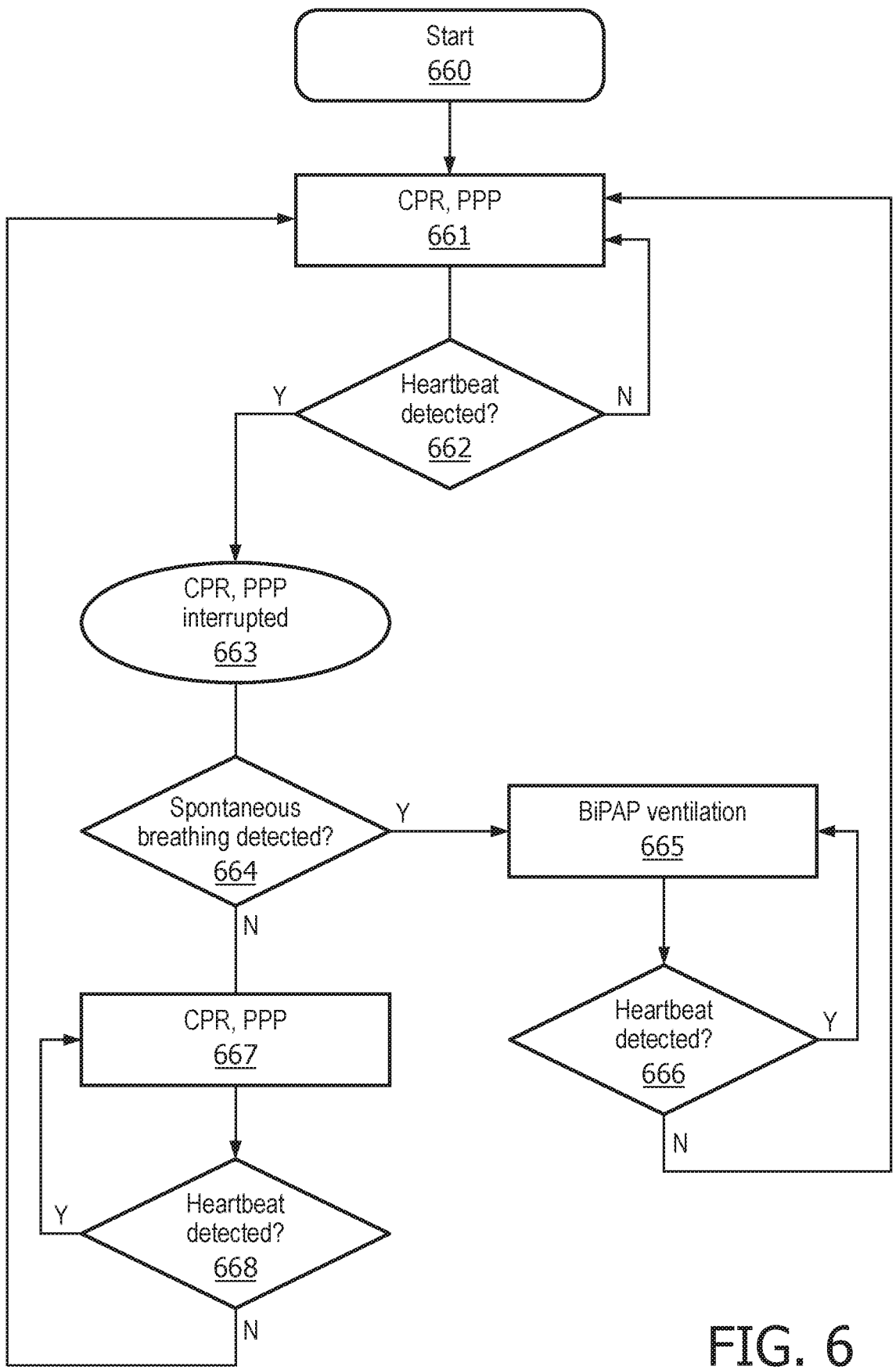
FIG. 6 is a flow diagram representing a method of operating a device according to an embodiment of the invention.

FIG. 6 shows a possible workflow for the use of a CPR device (not shown) according to an embodiment of the present invention, for example according to the embodiment of FIG. 4. At 660 the CPR device is started, after it has been connected to a subject, and after a sensor for detecting a subject's vital sign, in particular for detecting a subject's pulse, has also been connected to the CPR device and to the subject. Once started, the CPR device delivers air to the airways of the subject PPPs with an amplitude greater than 30 mbar and a frequency in a range of 40-240 beats per minute, in order to provide CPR, and at the same time delivers PPPs with a smaller amplitude than 30 mbar and a frequency in the range of 3 to 20 cycles per minute, in order to provide an assured airflow to the subject, as at 661. The CPR device will continue to operate in this mode until a heartbeat is detected by the sensor, as at 662; at this point CPR will be interrupted, as at step 663. This can happen automatically, or it can be manually operated by the operator; both possibilities are within the scope of the invention. For example, the recovered heart rate may be measured by a sensor, like sensor 140 of FIG. 1; sensor 140 can for example be an electrical sensor (like an ECG electrode), which is either integrated in the patient interface or attached to the subject's chest. Alternatively, the recovered heartbeat can be detected in the Photoplethysmographic signal of a finger PPG sensor, because the PPG signal of a natural heartbeat differ in timing and shape from the artificial pulsation generated by the CPR PPP. Once CPR PPP are stopped as at 663, assisted ventilation will continue until a spontaneous breathing is detected, as at step 664. A spontaneous breathing can be detected for example by including a flow and pressure meter in the device 661; detection of the onset of a spontaneous inspiration and/or expiration cycle is known to a person skilled in the art, for example from the CPAP/BiPAP systems of Philips/Respironics. Once spontaneous breathing is detected, the CPR device can switch to a BiPAP ventilation operation mode, which supports the spontaneous breathing of the subject, as at step 665. Also in this case, it is within the scope of the invention that such switching can happen automatically or manually. If no spontaneous breathing is detected, the CPR device will continue to operate, as at step 667, unless manually stopped by the operator. In all aforementioned situations, the sensor will continue monitoring the heartbeat, and as soon as another cardiac arrest or anomaly is detected, delivery of CPR will be started again, as at 666 and 668.

Figure 7:
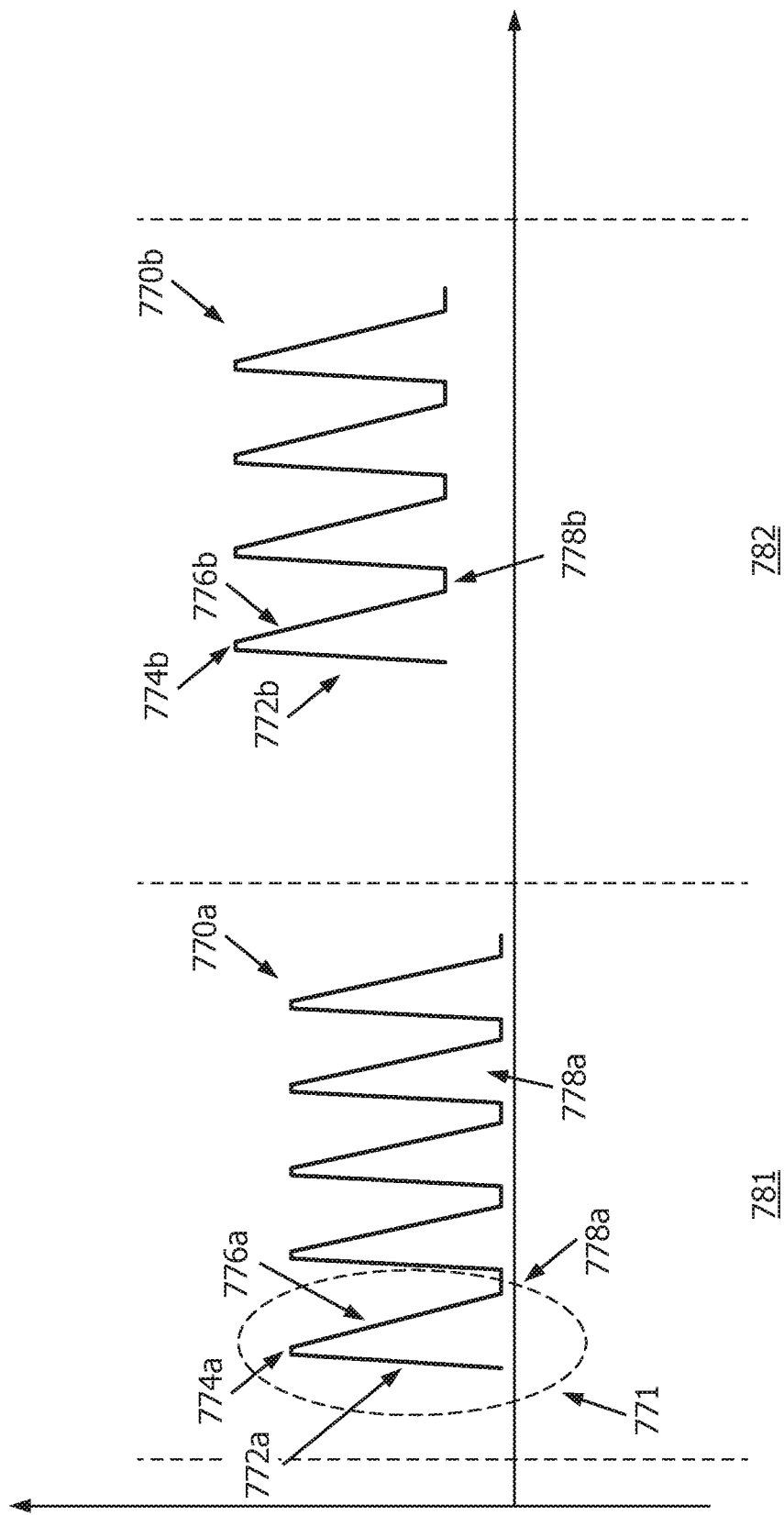
FIG. 7 is a graph representing the pressure profile of a possible PPP.

FIG. 7 shows a graph of possible outputs 770*a* and 770*b* of series of PPPs for inducing CPR according to the present invention. In the graph of FIG. 7, time is shown along the x-axis, and pressure along the y-axis. It is to be understood that the graph of FIG. 7, like the all others graph in this application, is not drawn to scale and it is merely used to help visualize what is written in the present description. Outputs 770*a* and 770*b* refers to lungs inflation phase 781 and lungs deflation phase 782, respectively. At the beginning of each complete PPP 771, the air pressure is rapidly increased to a maximum 774*a* or 774*b*, as indicated by the ascending portions 772*a* and 772*b*. The maximum pressure is maintained for a short period, which can be preset and varied according to the specific situation, until pressure is decreased again, as in 776*a* and 776*b*, typically in a less steep fashion when compared to rise 772*a* and 772*b*, and it reaches a minimum 778*a* or 778*b*. Shape, amplitude and length of each phase 772*a*-778*a* and 772*b*-778*b* can be modified by the caregiver using the device and are not limited to what is shown in FIG. 5. During lung deflation, it is preferable to generate PPPs of different absolute amplitude, in order to compensate for the change in ITP due to the reduced volume of the lungs. However, the invention contemplates all possible relationships between different PPPs.

FIG. 8*a* is a graph that shows the behavior of lungs volume 883 and of ITP 884 of a subject undergoing a typical volume assured mechanical ventilation. In the graph of FIG. 8, time is plotted along the x-axis, while flow and lung volume is plotted along the y-axis. Ventilator output 880 represents the output air flow of the air delivered by an air pressure/flow generator, for example air pressure generator 110-410, along the lung inflation phase 881 and the lung deflation phase 882. During inflation phase 881, the air pressure generator delivers a certain constant airflow to the lungs of the subject, normally in the order of 200 ml/sec. While air is delivered to the lungs at a constant airflow, the lungs inflate and therefore the lungs volume constantly increases, as shown by 883, until it reaches a peak when lung deflation 882 starts. As a consequence of the increase in volume, ITP pressure also increases in a fashion directly proportional to the increase in lung volume, as shown by 884. When lung deflation 882 starts, the air pressure generator decreases the delivered air pressure, consequentially allowing the lungs to deflate, because of the thoracic muscles and lungs resiliency, and decreasing lungs volume 883 and ITP 884 to a minimum when lungs deflation 882 ends and lungs inflation 881*a* starts again.

Figure 8B:
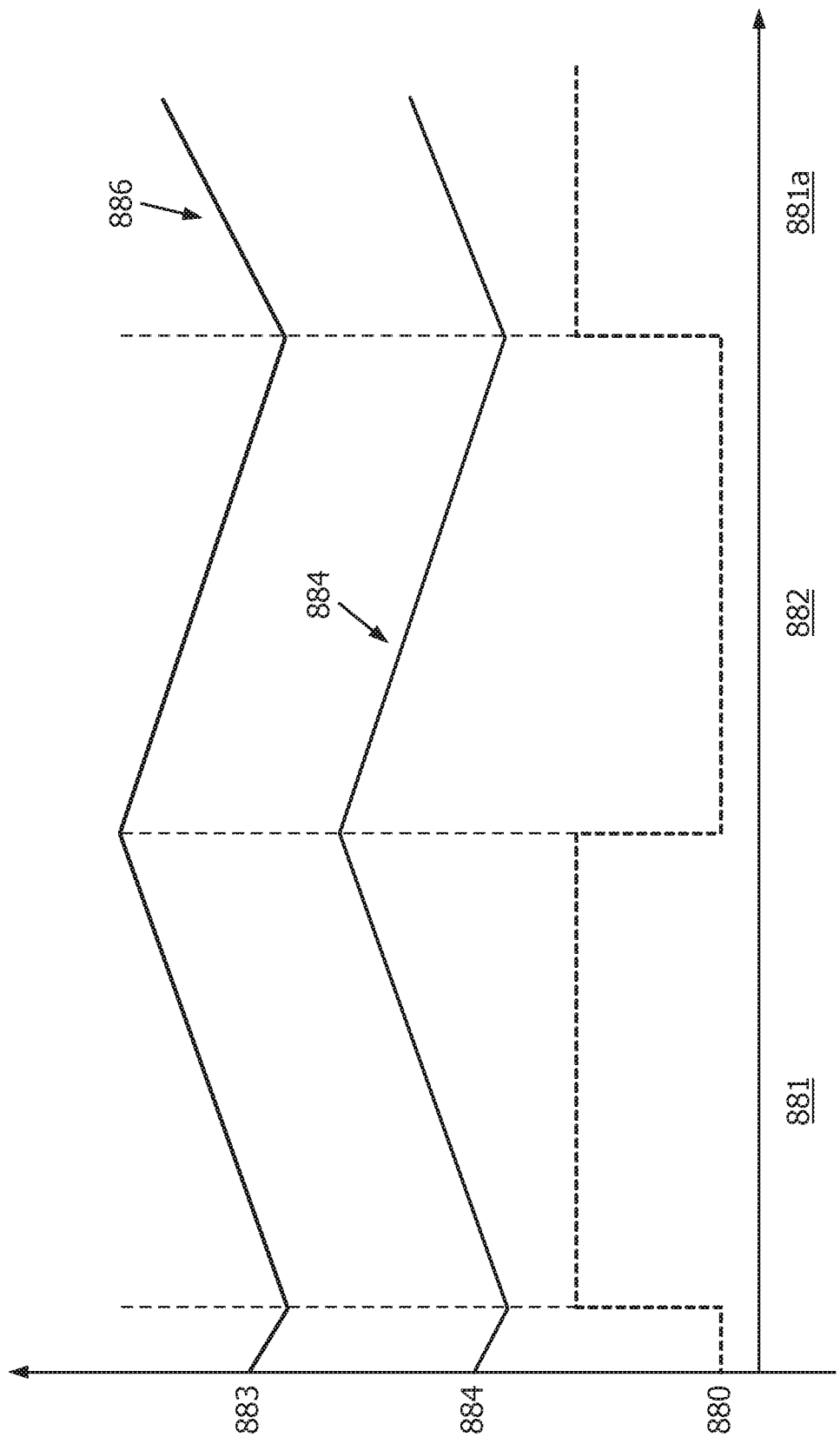
FIG. 8b is a graph showing the relationship between the flow delivered by a device according an embodiment of the invention and the variation in lung Volume and ITP during a positive pressure supported spontaneous breathing.

FIG. 8*b* is similar to FIG. 8*a*, wherein the lung and ITP profiles are shown for a subject undergoing a pressure assisted breathing instead of mechanical ventilation. The main difference in this embodiment is that ventilator output 880 represents the output pressure in the BiPAP mode of the air delivered by air pressure 110-410, instead of the output airflow. In BiPAP mode, during inflation phase 881, the air pressure generator delivers a certain constant positive pressure to the lungs of the subject, normally in the order of 20 mbar. Similarly to when volume assured mechanical ventilation is delivered, while air is delivered to the lungs at a constant pressure, the lungs, and therefore the lungs volume constantly increases, as shown by 883, until it reaches a peak when lung deflation 882 starts. As a consequence of the increase in volume, ITP pressure also increases in a fashion directly proportional to the increase in lung volume, as shown by 884. When lung deflation 882 starts, the air pressure generator decreases the delivered air pressure, consequentially allowing the lungs to deflate, because of the thoracic muscles and lungs resiliency, and decreasing lungs volume 883 and ITP 884 to a minimum when lungs deflation 882 ends and lungs inflation 881*a* starts again.

Figure 9:
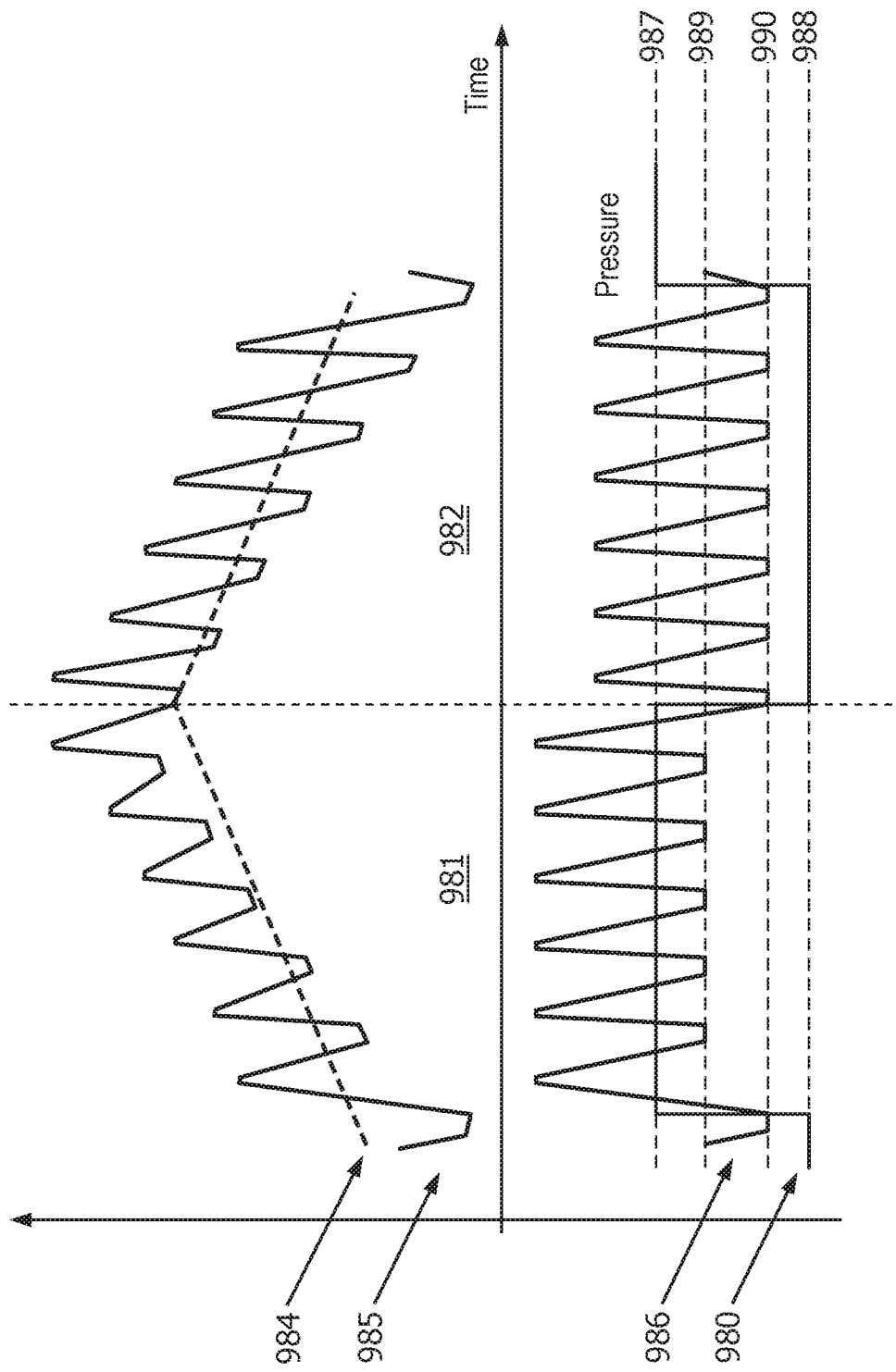
FIG. 9 is a graph showing the air volume profile of the mechanical ventilation device according to an exemplary embodiment of the invention.

FIG. 9 is a graph that shows ITP profile 985 when air pressure generator 110-410 is operated in the CPR mode and in the mechanical ventilation mode simultaneously (CPR/mechanical ventilation mode). In the graph of FIG. 9, time is shown along the x-axis, wherein inflation phase 981 is followed by deflation phase 982, while pressure and volume are both shown along the y-axis, as this is only an illustrative graph. Air pressure generator 110-410 output 986 is the result of the superposition of an output for delivering CPR, for example output 770 of FIG. 7, and of an output for delivering mechanical ventilation, for example output 980 shown in the same figure. Dashed lines 987 and 988 represents upper and lower baseline of output 980, respectively, while dashed lines 989 and 990 represents the corresponding baselines of output 986. In the context of the present application, by baseline it is meant the flow or pressure value of an output, for example output 980 and 986, in the absence of a PPP. Upper and lower baseline refer to the baseline during the inspiration and expiration phase, respectively. As represented in the graph of FIG. 9, baselines 987 and 988 of output 980 have a greater amplitude in absolute value then baselines 989 and 990 of output 986. The reason for this difference is hereby explained: mechanical ventilation is designed to provide to a subject's lungs an amount of air at least sufficient to completely inflate the lungs so that the oxygen and CO2 exchange is maximized. The total amount of air provided by a mechanical ventilator is equal to the area under the curve of the mechanical ventilator flow output graph, such as for example output 980. It is apparent from FIG. 9*a* that when PPPs are also delivered by the same device, for example device 100-400, an additional amount of air is supplied to the subject's lungs; the increase in the area under the curve can be seen for example by looking at output 986. For this reason, when a device according to the present invention is operating simultaneously the CPR and the mechanical ventilation functions, it is preferable to reduce the amplitude of the mechanical ventilation function, in order to avoid hyper-inflating the lungs excessively, which could be damaging for the lungs themselves and would prevent a sufficient venous backflow and a sufficient refilling of the atria, as the pressure would increase significantly. In mathematical terms, the total area under the curve of output 986 should be substantially similar to the area under the curve of output 980, or the typical output curve of a typical ventilator. This can be seen for example by observing the upper part of FIG. 9*a*, wherein profile 984 represents the ITP profile (or the profile of the lungs volume variation) during normal mechanical ventilation (similarly to line 884 in FIG. 8*a*), i.e. resulting from output 980, while profile 985 represents the ITP profile (or the profile of the lungs volume variation) resulting from output 986. When compared to profile 984, the larger area under the curve of profile 985 where PPPs are delivered is compensated by a smaller area in the pause periods between each PPP. Of course, instead of reducing the amplitude of the mechanical ventilation component, other adjustments can be contemplated, for example by using vent valves in the patient interface, or by having each PPP followed by a negative pressure pulse of similar magnitude, so that the air in excess is sucked out of the subject's lungs. Such adjustments can be done manually by the operator, they can be pre-set for the device, or they can also be imagined as an automatic change of setting triggered by the activation of the CPR function when the ventilation function is already active, for example when device 100-400 is used as a typical mechanical ventilator and a sudden cardiac arrest episode happens. In other embodiment of the invention, it is also possible to add a sensor capable of measuring the air pressure inside the lungs, for example a pressure sensor in the esophagus for a surrogate measure of the ITP, and set device 100-400 so that it automatically adjust in order not to exceed the maximum pressure tolerated by the lungs walls.

When air pressure generator 110-410 is operated in the CPR mode and in the assisted ventilation mode simultaneously (CPR/assisted ventilation mode), the ITP profile and lung volume profiles are similar to those shown in FIG. 9 for the CPR/mechanical ventilation mode. However, while in this operating mode it is difficult to measure the subject's spontaneous breathing effort and thus the subject's spontaneous airflow; moreover, this may change over time and cannot be predicted. As a consequence, in spontaneous breathing/CPR mode there is a risk to damage the lung due to hyperinflation or hypo-inflation; in such case, it is therefore preferable to set air pressure generator 110-410 such that the amplitude and the duration of the PPPs are reduced. Such adjustments can be done manually by the operator or it can be triggered automatically when the device switches to CPR/spontaneous breathing operating mode. In another embodiment, the device comprises change of CPR setting triggered by monitoring the lung inflation. In another embodiment of the invention, it is possible to add a pressure sensor in the esophagus of the subject in order to obtain a surrogate measure of the ITP, and the air pressure generator 110-410 is configured to automatically adjust its setting based on the measured ITP.

Figure 10:
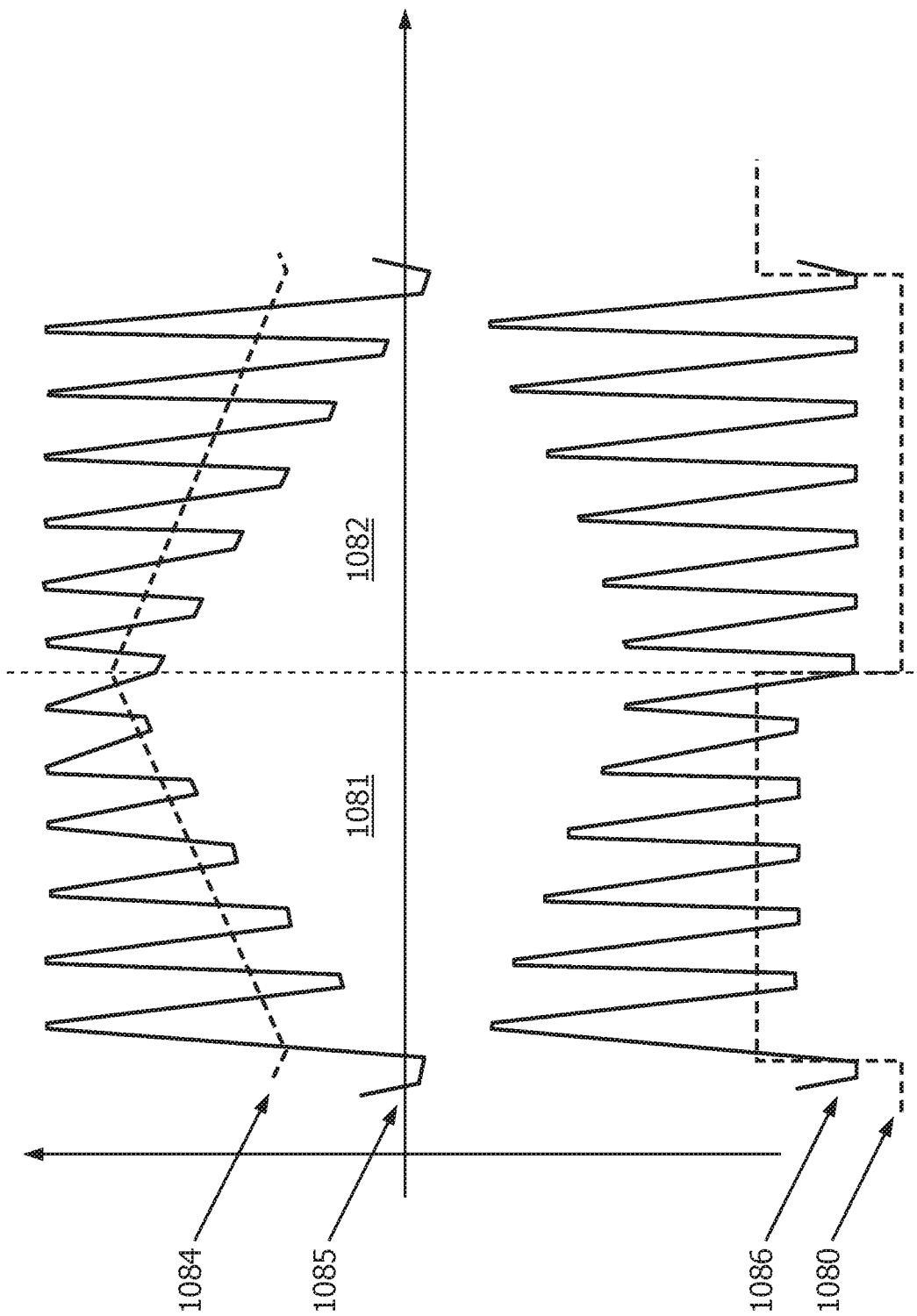
FIG. 10 is a graph showing the air volume profile of the mechanical ventilation device according to another exemplary embodiment of the invention.

FIG. 10 shows ITP profile 1085 according to another embodiment of the present invention. According to this embodiment air pressure generator 110-410 is operated in the CPR mode and in the mechanical or assisted ventilation mode simultaneously. In the graph of FIG. 10, time is shown along the x-axis, wherein inflation phase 1081 is followed by deflation phase 1082, while flow and pressure are shown along the y-axis. Similarly to the embodiment of FIG. 9, air pressure generator 110-410 output 1086 is the result of the superposition of an output for delivering CPR, for example output 770 of FIG. 7, and of an output for delivering mechanical or assisted ventilation, for example output 1080. Also similarly to FIG. 9, output 1086 baselines are adjusted to a lower absolute value so not to build-up an excessive pressure into the subjects' lungs; a typical ITP profile during simple mechanical ventilation is represented by profile 1084, for comparison purposes. The embodiment of FIG. 10 differs from that of FIG. 9 in that the peak ITP of all PPPs is substantially the same, as per profile 1085. An advantage of this embodiment is that the pressure delivered to the heart is constant. This is important in order to produce a regular CPR which is independent of the inflation or deflation phase of the lungs. In fact, it is apparent that the ITP generated by a PPP when the lungs are inflated is greater than the ITP generated when the lungs are less inflated, as it is clear by looking at FIG. 9. To compensate for this variations and to produce a constant peak ITP, device 100-400 can be set so that the amplitude of each PPP decreases as the lungs are inflated, and increases as the lungs are deflated. This can be set in advance, but it can also be made dependent on a sensor capable of measuring the ITP pressure as described above.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

The invention claimed is:

1. A cardiopulmonary resuscitation, CPR, device for delivering intrathoracic pressure pulses to a subject, the device comprising an air pressure generator for delivering air to the airways of the subject, wherein the air pressure generator is configured to:
   operate a first mode, wherein in the first mode the air pressure generator generates a first output comprising a first plurality of positive pressure pulses for temporally increasing the subject's intrathoracic pressure to induce compressions of the heart of the subject by increasing the volume of the subject's lungs;
   operate a second mode, wherein in the second mode the air pressure generator generates a second output comprising a second plurality of positive pressure pulses for providing an assured airflow to the lungs of the subject; and
   deliver a resulting output to the airways of the subject, the resulting output being the superposition of the first output and of the second output;
   wherein said first plurality of positive pressure pulses have an amplitude greater than 30 mbar and a frequency in a range of 40-240 beats per minute; and
   wherein said second plurality of positive pressure pulses have an amplitude smaller than 30 mbar and a frequency in a range of 3 to 20 cycles per minute.

2. A CPR device according to claim 1, wherein the air pressure generator is configured to operate the first mode and the second mode simultaneously.

3. A CPR device according to claim 1, wherein device is arranged for receiving a measured vital sign of the subject, the air pressure generator being arranged to deliver the first plurality of positive pressure pulses and/or the second plurality of positive pressure pulses in dependence of the measured vital sign.

4. A CPR device according to claim 3 wherein the amplitude and/or the frequency of the first plurality of positive pressure pulses and/or the second plurality of positive pressure pulses are dependent on the received measured vital sign.

5. A CPR device according to claim 3, wherein the device is configured to interrupt delivering air pressure pulses of said first plurality for a predetermined time, in order to check whether the received vital sign is in a pre-determined range, and wherein device is further configured to continue with delivering the air pressure pulses of said first plurality when the vital sign is not in the predetermined range during the predetermined time.

6. A CPR device according to claim 3, wherein the received vital sign is an ECG signal, wherein the device is arranged to obtain the ECG signal during the delivery of the air pressure pulses of said first plurality, the device being arranged to stop the delivery when the received ECG signal meets pre-determined criteria.

7. A CPR device according to claim 3, wherein the received vital sign is a respiratory signal for measuring subject's breathing performance.

8. A CPR device according to claim 7, wherein the device is arranged to use a measuring of a spontaneous breathing of subject to detect subject's pulse.

9. A CPR device according to claim 1, wherein device is arranged for receiving a measured intrathoracic pressure of the subject, and wherein the air pressure generator is further configured to set the amplitude of the positive pressure pulses of said first plurality in dependence of the measured intrathoracic pressure.

10. A CPR device according to claim 9, wherein the amplitude of the positive pressure pulses of said first plurality is set to produce a constant peak intrathoracic pressure.

11. A CPR device according to claim 1, wherein the air pressure generator is further configured to deliver a negative pressure pulse after a positive pressure pulse of said first plurality.

12. A CPR device according to claim 11, wherein said negative pressure pulse has an amplitude which is smaller than the amplitude of the positive pressure pulse of said first plurality.

13. A system for providing CPR comprising the CPR device according to claim 1, a patient interface coupled to the air pressure generator for providing the air pressure pulses to the respiratory tract of the subject and a sensor for measuring a vital sign of subject.

14. A system according to claim 13, wherein sensor is a Photoplethysmography, PPG, sensor.

15. A system according to claim 13, further comprising a sensor for measuring the intrathoracic pressure of the subject.

16. A method of operating an air pressure generator for delivering intrathoracic positive air pressure pulses to a subject, wherein the air pressure generator is capable of operating in a first and second mode, wherein each mode is characterized by generating air pressure according to a specific profile, said method comprising:
   activating a first operating mode, said first mode generating a first output, wherein said first output comprises a first plurality of positive pressure pulses for temporally increasing the subject's intrathoracic pressure to induce compressions of the heart of the subject by increasing the volume of the subject's lungs; and
   activating a second operating mode, said second mode generating a second output, wherein said second output comprises a second plurality of positive pressure pulses for providing an assured airflow to the lungs of the subject;
   wherein a resulting output generated by the air pressure generator is the superposition of the first output and of the second output;
   wherein said first plurality of positive pressure pulses have an amplitude greater than 30 mbar and a frequency in a range of 40-240 beats per minute; and
   wherein said second plurality of positive pressure pulses have an amplitude smaller than 30 mbar and a frequency in the range of 3 to 20 cycles per minute.

17. A computer program product comprising a computer readable medium having computer readable code embodied therein, the computer readable code being configured such that, on execution by a suitable computer, processor or controller that is for use with an air pressure generator for delivering intrathoracic positive air pressure pulses to a subject, the computer, processor or controller is caused to perform the method of claim 16.

* * * * *